(12) United States Patent
Lyon

(10) Patent No.: US 6,464,391 B2
(45) Date of Patent: Oct. 15, 2002

(54) HEAT RELEASE RATE CALORIMETER FOR MILLIGRAM SAMPLES

(75) Inventor: Richard E. Lyon, Absecon, NJ (US)

(73) Assignee: The United States of America as represented by the Secretary of Transportation, Washington, DC (US)

(*) Notice: Subject to any disclaimer, the term of this patent is extended or adjusted under 35 U.S.C. 154(b) by 21 days.

(21) Appl. No.: 09/741,871

(22) Filed: Dec. 22, 2000

(65) Prior Publication Data

US 2002/0080849 A1 Jun. 27, 2002

(51) Int. Cl.$^7$ .................. G01K 17/00; G01N 25/22
(52) U.S. Cl. ................. 374/36; 374/45; 374/14; 422/51; 436/157; 436/160
(58) Field of Search .............. 374/45, 31, 14, 374/36; 436/157, 147, 155, 160; 422/51

(56) References Cited

U.S. PATENT DOCUMENTS

| | | | | |
|---|---|---|---|---|
| 2,458,610 A | * | 1/1949 | Lindstrom | 436/160 |
| 3,096,157 A | * | 7/1963 | Brown et al. | 436/160 |
| 3,853,474 A | * | 12/1974 | Austin | 436/160 |
| 3,933,429 A | * | 1/1976 | Shibata et al. | 436/160 |
| 4,229,967 A | * | 10/1980 | Kneifel et al. | 73/15 R |
| 4,499,191 A | * | 2/1985 | Bruning et al. | 436/160 |
| 4,761,078 A | | 8/1988 | Farris et al. | |
| 5,235,862 A | * | 8/1993 | Harada | 436/157 |
| 5,981,290 A | | 11/1999 | Lyon et al. | |
| 6,312,154 B1 | * | 11/2001 | Schick et al. | 374/36 |
| 6,371,147 B1 | * | 4/2002 | Philippe | 137/6 |
| 2001/0018218 A1 | * | 8/2001 | Ragaglia et al. | 436/160 |

FOREIGN PATENT DOCUMENTS

| | | | | |
|---|---|---|---|---|
| JP | 0173466 | * | 9/1985 | 436/160 |
| JP | 3009861 | * | 1/1988 | 436/157 |

OTHER PUBLICATIONS

Microscale Combustion Calorimeter DOT/FAA/AR–01/117 Final Report Feb. 2002.
Lyon, Solid–State Thermochemistry of Flaming Combustion, appearing as Chapter 11 in *Fire Retardancy of Polymeric Materials*, edited by Grand, et al.; Marcel Dekker, Inc., 2000.
Reshetnikov, et al., Oxidation kinetic of volatile polymer degradation products, Polymer Degradation and Stability 64 (1999).
Gracik, et al., A novel thermogravimetric technique for determining flammability characteristics of polymeric materials, *Thermochimica Acta*, 212 (1992).

(List continued on next page.)

*Primary Examiner*—Diego Gutierrez
*Assistant Examiner*—Gail Verbitsky
(74) *Attorney, Agent, or Firm*—James J. Drew; Otto M. Wildensteiner

(57) ABSTRACT

A calorimeter that measures heat release rates of very small samples (on the order of one to 10 milligrams) without the need to separately and simultaneously measure the mass loss rate of the sample and the heat of combustion of the fuel gases produced during the fuel generation process. The sample is thermally decomposed in a small volume pyrolysis chamber. The resulting fuel gases are immedediately swept by an inert gas stream from the pyrolysis chamber into a combustion furnace in a plug-like flow. This plug flow substantially synchronizes the emerging fuel gases with the mass loss rate of the sample. Oxygen is metered into the fuel gas stream just before it enters the combustion furnace where the fuel gases are completely oxidized. The effluent from the furnace is analyzed to determine the amount of oxygen consumed per unit time and the heat release rate is computed without the need to separately measure the mass loss rate of the sample.

6 Claims, 3 Drawing Sheets

OTHER PUBLICATIONS

Parker, Determination of the Input Data for a Model of the Heat Release Rate of Wood, *Special Technical Publication 983* (1988), American Society for Testing and Materials.

Susot, Characterization of the Thermal Properties of Forest Fuels by Combustible Gas Analysis, *Forest Science*. vol. 28, No. 2 (1982), Society of American Foresters.

Susot, et al., A Quantitative Thermal Analysis Technique for Combustible Gas Detection, *Journal of Fire & Flammability*, vol. 10 (Apr. 1979).

Lyon, et al., A Pyrolysis–Combustion Flow Calorimeter Study of Polymer Heat Release Rate, a paper presented at the Ninth Annual BCC Conference on Flame Retardancy, Jun. 1998.

Kifer, et al., Thermal Evolution Analysis of Some Organic Materials, *Analytic Calorimetry*, 1974.

* cited by examiner

HEAT RELEASE RATE CALORIMETER FOR MILLIGRAM SAMPLES

The invention described herein may be manufactured, used, and licensed by or for the Government of the United States without the payment to me of any royalties thereon.

FIELD OF THE INVENTION

The present invention relates generally to calorimeters, and more particularly to calorimeters used to measure heat release rates of small samples. Such calorimeters are useful in determining flammability parameters of milligram samples of combustible materials.

BACKGROUND OF THE INVENTION

The rate at which heat is released during the burning of a combustible solid in a fire is the primary indicator of its hazard to life and property. Consequently, a method to study the heat release rate of solids in a fire or under fire conditions is of theoretical and practical importance to fire protection engineers and materials scientists. Fire calorimeters are used to measure the rate of heat released in flaming combustion, often with simultaneous measurement of the fuel generation (mass loss) rate of the solid. Since the combustion reactions in the flame are orders of magnitude faster than the fuel generation rate of the solid and the transit time of the gaseous fuel between the burning surface and the flame where combustion occurs is less than one second, the slow step (that is, the step limiting the burning rate in flaming combustion of solids) is the fuel generation rate. This means that the heat released in flaming combustion is essentially simultaneous with, and proportional to, the mass loss of the solid, and that the heat release rate in a fire is simultaneous with, and proportional to, the mass loss rate at the surface of the material.

Fire calorimeters measure the heat release rate in flaming combustion directly but have drawbacks for materials research or quality control testing. These drawbacks include: 1) the heating rate in the sample varies with location; 2) the temperature of the sample is non-uniform because of thickness and edge effects; 3) the amount of oxygen diffusing into the flame is usually less than is required to effect complete combustion of the fuel gases, so that measured heat release rate depends on the test environment; 4) the measured heat release rate depends on the sample thickness, orientation, and method of holding the sample, (i.e., on the test method); 5) fire calorimeters give qualitative (about 15% error) rather than quantitative (about 5% error, or less) heat release rate data because of the poor repeatability of the test as a result of drawbacks 1) through 4) above; 6) samples must be large (on the order of about 100 grams) to support steady flaming combustion: and 7) replicate samples are needed because of the poor repeatability of fire calorimetry tests. Thermoformed kilogram samples are impractical for research where initial synthesis of new materials typically yields one (1) gram of material. Gram quantities of sample can be used for ease of ignition (flammability) tests utilizing a Bunsen burner but only pass/fail results are obtainable and reproducibility is poor.

Because flaming combustion requires large samples and the thermal history and combustion environment vary from sample to sample, fire calorimetry is not the method of choice for measuring the fire performance properties of materials. Likewise, ignitability tests provide only relative rankings but no properties that can be related to fire performance. A number of thermoanalytical methods have been developed which use thermal decomposition of milligram-sized samples and analysis of the evolved gases to measure the heat released under controlled (laboratory) conditions. Of those known laboratory thermoanalytical methods which have been used to measure the non-flaming heat of combustion of the sample gases under simulated fire conditions, all measure the total heat of combustion of the sample pyrolysis (fuel) gases. However, only the methods that measure the mass loss rate of the sample can determine heat release rate of an individual material particle (specific heat release rate) as it occurs at a burning surface in a fire. The heat release rate in a fire during steady flaming combustion is equal to the specific mass loss rate (rate at which the solid particle decomposes into fuel which can enter the gas phase/flame) multiplied by the thickness of the surface burning layer (number of solid particles involved), the heat of combustion of the particles (heat released per particle by complete combustion), and the efficiency of the combustion process in the flame (fraction of solid particles which enter the gas phase and are completely combusted). Because the rate of mass loss at the burning surface is a relatively slow process in comparison to the gas phase combustion reactions, the heat release in a fire is coincident in time with, and proportional to, the mass loss (fuel generation) rate of the sample. Consequently, unless the evolved gas measurement is synchronized with the sample mass loss in a laboratory test, the heat release rate as it occurs in a fire cannot be measured. One approach to obtain the rate of heat released by the sample under fire conditions is to measure mass loss (fuel generation) rate and heat of combustion of the fuel gases separately and then multiply them together.

Lyon and Walters have invented and patented a microscale combustion calorimeter that measures flammability parameters of milligram samples of combustible materials. U.S. Pat. No. 5,981,290. In order to obtain results consistent with other techniques, the invention requires the simultaneous measurements of the mass loss rate of the sample, and the amount of oxygen consumed by combustion of the fuel gases given off by the sample. The mass loss rate is measured by using a thermogravimetric analyzer (TGA), while the amount of oxygen consumed is measured using a mass flow meter and oxygen analyzer downstream from the combustor.

Errors of more than 50% result when the heat release rate of the sample is determined solely from the oxygen consumption rate without a mass loss rate measurement. These errors arise principally from two sources: (1) distortion of the heat release rate curve and (2) reduced area under the heat release rate curve. Each of these sources of error will be discussed in turn.

DISTORTION OF THE HEAT RELEASE RATE CURVE: The mass loss (fuel generation) event for a rapidly heated small sample of combustible material occurs over a narrow time interval. The mass loss/fuel generation rate versus time curve has the form of a narrow peak or "fuel pulse". Multiple fuel pulses are observed for multi-component materials. The shape of the fuel pulse is unique to a particular material or component. This fuel pulse becomes spread out, broadened, or "smeared" if it is generated in a large volume (e.g., the pyrolysis chambers of commercial thermogravimetric analyzers) where the fuel gases can be intermingled, mixed, and diluted with the purge gas before exiting to the combustion chamber or furnace. This same intermingling, mixing, and dilution occurs anywhere in the flow calorimeter where a large volume is introduced (e.g., the scrubbers). The large volume of the TGA has the effect of distorting the shape of the fuel pulse prior to its reaction with oxygen in the combustor or furnace. Large volumes further downstream distort the shape of the combustion gases before the oxygen content of the combustion products can be measured. Consequently, the oxygen consumption history measured at the downstream oxygen detector has been distorted by the instrument and is not synchronized with the fuel pulse of the material. In particular, instrumental broadening or smearing reduces the height and increases the width (duration) of the fuel pulse as deduced from oxygen consumption.

Of particular interest to fire scientists is the peak specific heat release rate of the sample (W/g). The peak specific heat release rate of a material is a quantitative measure of its fire hazard and is obtained by multiplying the height of the fuel pulse (maximum fuel generation rate, g/g–s) by the instantaneous heat of combustion of the fuel (J/g) at peak mass loss rate. The average heat of combustion of the fuel is proportional to the area under the oxygen consumption curve and is unaffected by instrumental broadening of the fuel pulse. The instantaneous heat of combustion of the fuel gases given off at peak mass loss rate cannot be determined, however, unless the oxygen consumption rate and mass loss rate are synchronized.

In the Lyon and Walters patent cited, the TGA is a Perkin-Elmer TGA System 7 with a pyrolysis chamber volume of approximately V=50 cubic centimeters (50 cm$^3$) which is typical of commercial TGA's. The residence time of the pyrolysis gases in the pyrolysis chamber is V/F where F is the volumetric flowrate of the purge gas entering the pyrolysis chamber. In the invention as practiced by Lyon and Walters F=100 cm$^3$ per minute and V=50 cm$^3$ so the residence time of the fuel gases in the pyrolysis chamber is V/F=(50 cm$^3$)/(100 cm$^3$/min)=0.5 minutes=30 seconds. During this residence time of 30 seconds in the pyrolysis chamber pyrolysis products are continuously intermingled, mixed, and diluted with the entering purge gas (typically nitrogen) before exiting to the combustor, flow meter and oxygen analyzer. Errors arise because this residence time in the pyrolysis chamber is long compared to the time interval $\Delta t$ over which the fuel gases are generated during the heating program, i.e., the fuel pulse width. The fuel pulse width is related to the temperature range over which the sample decomposes AT and the heating rate R as $\Delta t=\Delta T/R$. In the invention practiced by Lyon and Walters the typical heating rate is R=100 K/min and the typical pyrolysis temperature interval is $\Delta T$=50 K, so that the time interval over which fuel gases are produced (i.e., the fuel pulse width) is $\Delta t=\Delta T/R=$ (50 K)/(200 K/min)=0.25 minutes=15 seconds. The long residence time of the fuel gases in the pyrolysis chamber (30 seconds) relative to the fuel pulse width (15 seconds) results in the fuel gases being intermingled, mixed, and diluted with the purge gas before exiting. These effects distort (smear) the fuel pulse and the associated oxygen consumption history. Thus, for typical TGA pyrolysis chambers the fuel generation (mass loss) history is not coincident with, and proportional to, the oxygen consumption history, so the oxygen consumption history cannot be used to determine the heat release rate of the sample as occurs in the pyrolysis chamber or in a fire.

REDUCED AREA UNDER THE HEAT RELEASE RATE CURVE: High molecular weight organic compounds (tars) are fuels of low volatility (high boiling temperature) produced during polymer thermal decomposition. In fires where surface temperatures are high (ranging from about 400° C. to about 800° C.) these tars are gaseous and contribute substantially to the heat release rate in flaming combustion. In commercial thermogravimetric analyzers the pyrolysis chamber wall temperature is substantially lower than the boiling temperature of these tars. As a result, the tar tends to condense on the pyrolysis chamber wall as a liquid and is not transported in the gas stream which enters the combustor for reaction with oxygen. This results in less oxygen consumption and low apparent total heat release values (area under the heat release rate versus time curve).

For the foregoing reasons, there is a need for a calorimeter that can more accurately measure the heat release rate of milligram samples of materials.

OBJECTS OF THE INVENTION

Accordingly, it is an object of the present invention to provide a means and method for accurately measuring flammability parameters of milligram samples of combustible materials.

It is a further object of the present invention to provide a means and method for accurately measuring the heat release rates of milligram samples of combustible materials without the need to simultaneously measure the mass loss rate of the sample and the heat of combustion of the fuel gases.

It is a further object of the present invention to provide a means and method for measuring the heat release rate of milligram samples of combustible materials using a flow calorimeter with minimal distortion of the fuel gas profile produced by the pyrolyzation of the sample.

It is a still further object of the present invention to provide a means and method for measuring the heat release rate of milligram samples of combustible materials using a flow calorimeter and a simple analytical relationship applied to measured oxygen gas consumption.

It is a still further object of the present invention to provide a means and method for measuring the heat release rate of milligram samples of combustible materials using a flow calorimeter in which all the products of pyrolysis are captured and analyzed.

SUMMARY

Briefly, the present invention is a calorimeter that measures heat release rates of very small samples (on the order of one to 10 milligrams) without the need to separately and simultaneously measure the mass loss rate of the sample and the heat of combustion of the fuel gases produced during the mass loss process. This is accomplished by minimizing the size of the pyrolysis chamber so that the fuel gases are not intermingled nor diluted by the purge gas but instead travel through the instrument as a small plug of fuel gases. Eliminating the TGA, with its relatively large volume, reduces the pyrolysis volume, and thereby eliminates the need for the TGA in the first place. Eliminating the TGA has at least two advantages. First, it prevents the condensation of tars produced in the pyrolysis chamber and permits these high molecular weight fuels to contribute to the total combustion of the pyrolysis products. Second, this minimal intermingling of the fuel gases and dilution by the purge gas, enhances "plug flow" through the instrument, effectively synchronizing the oxygen consumption history with the sample mass loss history. Such synchronization permits a simple mathematical relation between the two quantities and the desired heat release rate of the sample.

DETAILED DESCRIPTION

Figure 1:
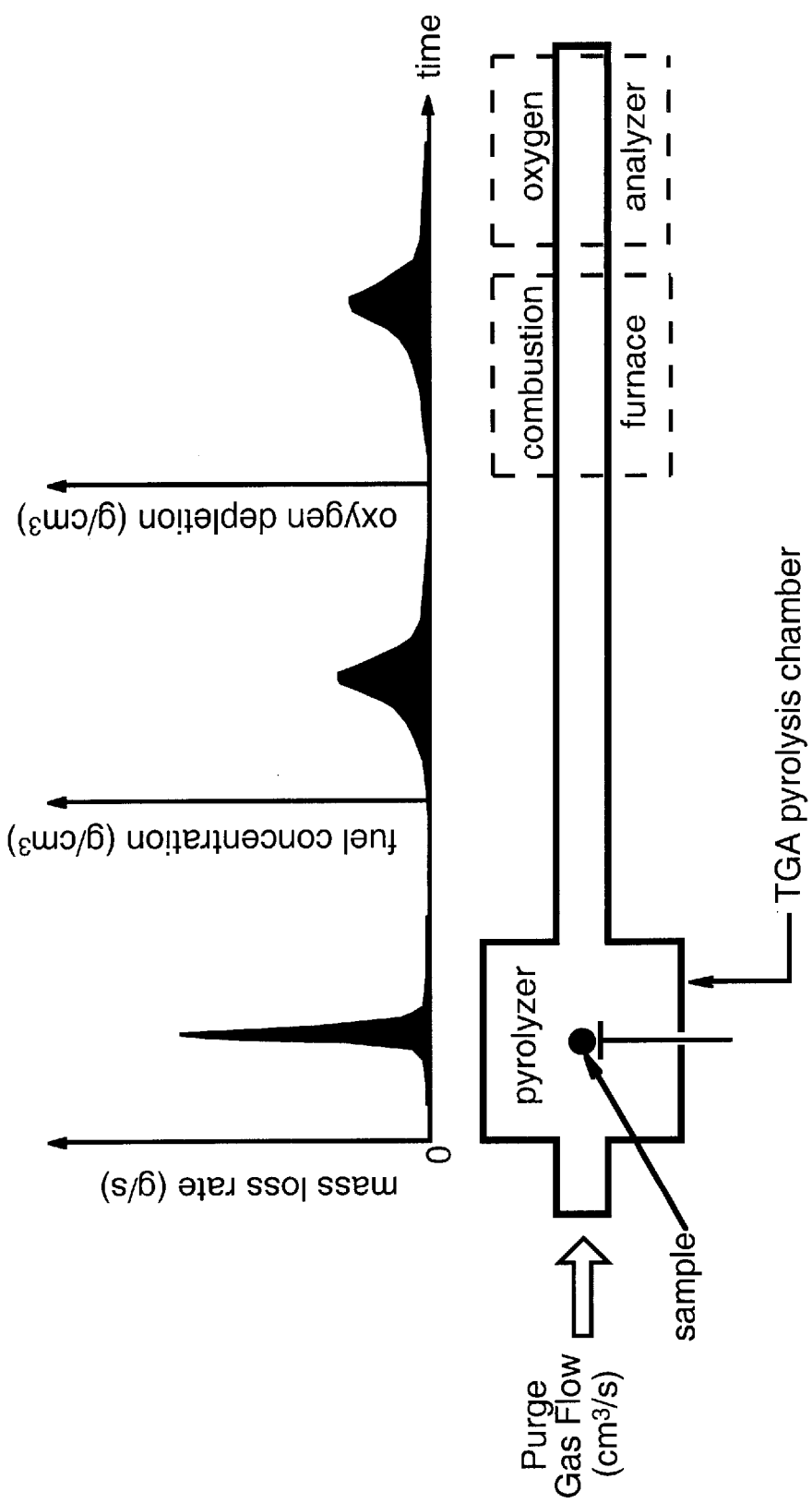
FIG. 1 is an idealized representation of an earlier calorimeter illustrating the fuel generation rate (mass loss rate) profile, the fuel concentration profile prior to entering the combustion chamber, or furnace, and the oxygen depletion profile of the gases emerging from the furnace.

In FIG. 1, a sample is pyrolyzed in a conventional thermogravimetric analyzer; the fuel gases produced by the pyrolysis are carried through a narrow tube by an inert purge gas toward a combustion chamber; a constant flow of oxygen sufficient to completely oxidize the fuel gases is metered into the gas stream, and then the fuel gases, the purge gas, and the oxygen are conducted into a combustion chamber where the fuel gases are completely oxidized. The oxygen depletion is measured over time to determine the rate at which fuel was generated by the pyrolysis of the sample. Because the oxygen depletion profile is "smeared" with respect to the fuel concentration profile, the simultaneous measurement of the mass loss rate of the sample is needed to accurately measure the fuel generation rate using this approach.

Figure 2:
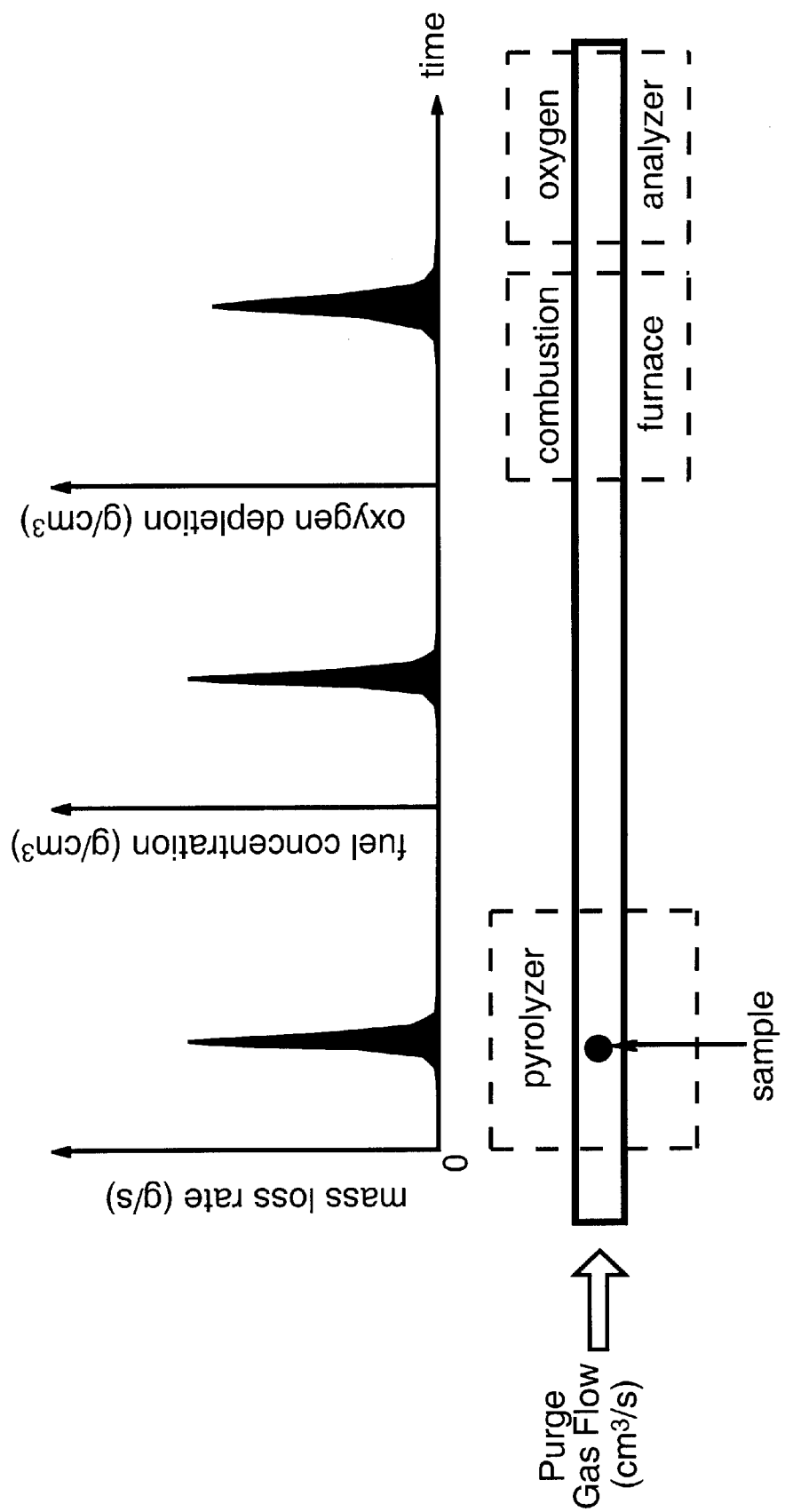
FIG. 2 is an idealized representation of one embodiment of the invention illustrating the fuel generation rate (mass loss rate) profile, the fuel concentration profile prior to entering the combustion chamber (or furnace), and the oxygen depletion profile of the gases emerging from the furnace.

In FIG. 2, the TGA, with its associated large volume, has been removed. Immediately, the problem of tar condensation on the walls of the TGA is eliminated. All of the fuel gases are then carried, synchronized with the sample mass loss rate, within the tube in a "plug-like" flow with greatly reduced intermingling, mixing, and dilution with the purge gas. Oxygen is metered into the plug as it enters the combustion chamber. The oxygen depletion profile mimics the fuel concentration profile, and also, the mass loss rate profile. The strong similarity of the oxygen depletion profile to the fuel concentration profile suggests that the events are synchronized and, consequently, the need to separately measure the mass loss rate is eliminated.

Figure 3:
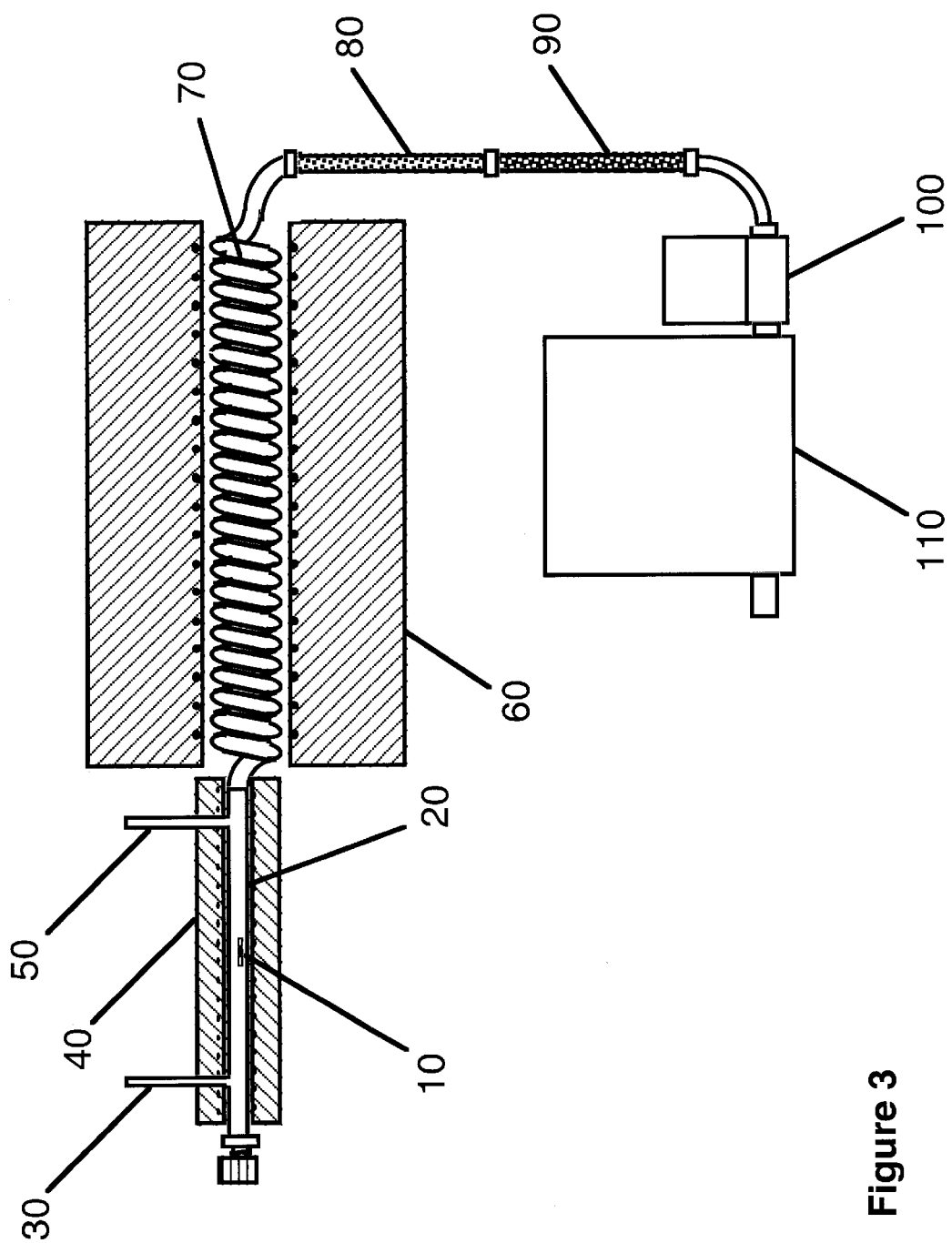
FIG. 3 is a schematic representation of one embodiment of the invention.

In FIG. 3, sample 10 is thermally decomposed (pyrolyzed) in small diameter pyrolysis tube 20 through which flows an inert purge gas (e.g., $N_2$) introduced through purge gas inlet tube 30. Typically, pyroloysis tube 20 is a quarter-inch (outer diameter) Inconel™ or similar tube about 6 inches long. Pyrolysis tube 20 runs through an electrical heater that raises the temperature of the sample. In this embodiment, the temperature increase is monotonic, but that is not necessary. As sample 10 is thermally decomposing, it produces fuel gases (products of decomposition), that are oxidized by mixing with a measured amount of oxygen or air introduced through oxidizer gas inlet 50. Oxidation takes place in combustion tube coil 70 that has an extended length of more than 12 inches, typically, 16 feet. Combustion tube coil 70 can also be fabricated from quarter-inch Inconel™ or similar tubing that is heat and chemical resistant. Combustion tube coil 70 is enclosed in insulated combustion furnace 60 where the fuel gases and oxidizer are heated to high temperature to convert the gases to stable carbon and hydrogen oxides (i.e., $CO_2$ and $H_2O$) and possibly acid gases (e.g., HCl, HF, $H_2SO_4$, etc). The combustion products are led from combustion furnace 60 through one or more condensers, filters, or scrubbers 80 and 90 that remove unwanted combustion products from the emerging gas stream, or effluent, leaving, in essence, only the inert purge gas and unreacted oxygen in the resulting stream. In one embodiment of the invention, the combustion products enter Drierite™ adsorbent tube 80 that removes $H_2O$ from the combustion products, and then through Ascarite™ adsorbent tube 90 that removes $CO_2$ and acid gases from the combustion products. Each of these scrubbers, 80 and 90, are about 6 inches long. Mass flow meter 100 is positioned in the gas flow to measure the mass flow rate of the remaining $N_2$ and $O_2$. The oxygen consumed from the gas stream by the oxidation (combustion) reactions is measured at an oxygen analyzer 110 located downstream from the scrubbers 80 and 90. The heat given off by oxidation/combustion of the gases is related to the oxygen consumed in the reactions by an empirical relationship that is well known in the art. Because oxygen analyzer 110 is located downstream from the sample, intermingling, mixing, and diffusion of the combustion gases, nitrogen carrier gas, and remaining oxygen occurs as the flow stream moves through the furnace and scrubbers to the oxygen analyzer. This journey causes the oxygen-time signal to be distorted or "smeared" with respect to the heat release rate of the sample. By minimizing the volume of pyrolysis tube 20, this smearing can be reduced. This desired flow through the calorimeter can be designated "plug flow" where the gases that emerge from the pyrolyzer enter the combustion furnace in the order in which they were produced by the thermally decomposing sample. The fuel gases are arranged from leading edge to trailing edge in a substantially linear distribution, essentially synchronized with the mass loss rate of the sample, according to the order and time when they were liberated in pyrolysis. The present invention maintains substantial plug flow of the fuel and subsequent combustion gases through the combustion calorimeter such that every element of the fuel and subsequent combustion gases has exactly the same residence time in the calorimeter. Consequently, the oxygen consumption pulse shape closely approximates the heat release rate pulse shape of the sample. Since the oxygen consumption pulse is now only slightly distorted with respect to the heat release rate of the sample, standard mathematical transforms can be used to reconstruct the heat release rate pulse from the oxygen consumption-time data. Such mathematical transforms are well-known in the art.

The mathematical transform function that eliminates the distortion in the oxygen consumption pulse shape may be integrated into the oxygen analyzer 110 to directly yield the heat release rate from the oxygen consumption pulse.

I claim:

1. A heat release rate calorimeter providing a quantitative measure of combustion dynamics of a sample comprising:
   a. means for thermally decomposing said sample under anaerobic conditions to produce fuel gases;
   b. a furnace for combusting said fuel gases;
   c. a stream of inert gas for transporting said fuel gases to said furnace in the order in which said fuel gases were produced by said thermally decomposing sample;
   d. a tube for conducting said fuel gases from said thermal decomposing means to said furnace, said tube confining said gas stream and said fuel gases in substantial plug flow;
   e. means for inserting a measured amount of oxygen into said inert gas stream and said fuel gases prior to combustion in said furnace;
   f. means for collecting the gaseous effluent from said furnace;
   g. means for measuring the amount of oxygen present per unit time in said effluent; and, h. means for applying a mathematical transform to compute the heat release rate of said sample from said measured amount of oxygen inserted into said fuel gases and inert gas stream and the measurement of the amount of oxygen present per unit time in said effluent.

2. A flow calorimeter for measuring the heat release rate of a sample in the milligram range comprising:
   a. A pyrolysis chamber for thermally decomposing said sample under anaerobic conditions to produce fuel gases;
   b. a furnace for combusting said fuel gases;
   c. a nitrogen gas stream for transporting said fuel gases to said furnace in the order in which said fuel gases were produced by said thermally decomposing sample;
   d. a narrow tube for conducting said fuel gases to said furnace, said tube confining said nitrogen and said fuel gases in a nitrogen/fuel gas stream in substantial plug flow;
   e. means for injecting oxygen at a measured rate into said nitrogen/fuel gas stream prior to combustion in said furnace;
   f. means for collecting the gaseous effluent from said furnace after combustion;
   g. means for removing unwanted substances from said effluent to produce a filtered effluent;
   h. means for measuring the oxygen content of said filtered effluent; and,
   i. means for applying a mathematical transform to compute the heat release rate of said sample by comparing the amount of oxygen injected into the nitrogen/fuel gas stream prior to combustion with the oxygen content of said filtered effluent.

3. The calorimeter as in claim 2 wherein the said filtered effluent consists essentially of nitrogen and oxygen.

4. The calorimeter as in claim 3 wherein said narrow tube has a cross-sectional dimension significantly less than its length.

5. A method for providing a quantitative measure of combustion dynamics of a sample, comprising the steps of:
   a. thermally decomposing said sample to fuel gases under anaerobic conditions;
   b. transporting in an inert gas stream said fuel gases in the order in which said fuel gases were produced by said thermally decomposing sample to a furnace;
   c. inserting a measured amount of oxygen into said fuel gases and said inert gas stream prior to combustion in said furnace;
   d. conducting said fuel gases and said inert gas stream to said furnace in a narrow tube that confines said fuel gases and said inert gas stream in plug flow;
   e. combusting said fuel gases in said furnace;
   f. collecting the gaseous effluent from said furnace after combustion;
   g. measuring the amount of oxygen present per unit time in said effluent; and,
   h. computing the heat release rate of said sample from said measured amount of oxygen inserted prior to combustion and the measurement of the amount of oxygen present per unit time in said effluent by applying a mathematical transform.

6. A method of measuring the heat release rate of a sample in the milligram range comprising the steps of:
   a. thermally decomposing said sample under anaerobic conditions in a pyrolysis chamber to produce fuel gases;
   b. transporting by means of a nitrogen gas stream said fuel gases in the order in which said fuel gases were produced by said thermally decomposing sample to a furnace;
   c. confining said fuel gases and said nitrogen gas stream from said pyrolysis chamber to said furnace in substantial plug flow within a small volume tube;
   d. injecting a measured amount of oxygen into said fuel gases and nitrogen gas stream prior to combustion in said furnace;
   e. combusting said fuel gases in said furnace;
   f. collecting the gaseous effluent from said furnace after combustion;
   g. removing unwanted substances from said effluent to produce a filtered effluent consisting essentially of said nitrogen gas stream and oxygen;
   h. measuring the oxygen content of said filtered effluent; and,
   i. comparing the said measured amount of oxygen injected prior to combustion with the oxygen content of said filtered effluent to calculate the heat release rate of said sample by applying a mathematical transform.

* * * * *